United States Patent [19]
Waterman

[11] Patent Number: 5,621,181
[45] Date of Patent: Apr. 15, 1997

[54] PROBE ASSEMBLY SYSTEM, INSERTION AND RETRIEVAL TOOL THEREFOR, AND METHODS

[75] Inventor: David K. Waterman, Santa Fe Springs, Calif.

[73] Assignee: Erico International Corporation, Solon, Ohio

[21] Appl. No.: 503,883

[22] Filed: Jul. 18, 1995

[51] Int. Cl.⁶ .................................. G01N 17/00
[52] U.S. Cl. ........................................... 73/866.5
[58] Field of Search ...................... 73/86, 863.82, 73/863.85, 866.5; 137/317; 29/252

[56] References Cited

U.S. PATENT DOCUMENTS

| | | | |
|---|---|---|---|
| 3,007,340 | 11/1961 | Kraftson | 73/866.5 |
| 3,247,721 | 4/1966 | Johnson | 73/863.82 |
| 3,718,034 | 2/1973 | Swearingen | 73/86 |
| 3,812,722 | 5/1974 | Soudelier | 73/422 |
| 4,275,592 | 6/1981 | Atwood et al. | 73/432 R |
| 4,346,611 | 8/1982 | Welker | 73/863.86 |
| 4,387,592 | 6/1983 | Welker | 73/198 |
| 4,537,071 | 8/1985 | Waterman | 73/432 R |
| 4,602,727 | 7/1986 | Spiegelman et al. | |
| 4,697,465 | 10/1987 | Evans et al. | 73/866.5 |
| 4,841,787 | 6/1989 | Waterman | 73/866.5 |
| 4,916,797 | 4/1990 | Strommen et al. | 29/426.5 |
| 4,930,361 | 6/1990 | Nimberger | 73/864.62 |
| 5,106,580 | 4/1992 | Mudiam | 422/53 |
| 5,138,755 | 8/1992 | Evans et al. | 29/263 |
| 5,146,083 | 9/1992 | Zuckerwar et al. | |
| 5,385,060 | 1/1995 | Wang | 73/866.5 |

OTHER PUBLICATIONS

Rohrback Cosasco Systems, Inc., Bulletin #652-B, "Model RBS COSASCO® Two-Inch System Retriever Kit".

*Primary Examiner*—Robert Raevis
*Attorney, Agent, or Firm*—Renner, Otto, Boisselle, Sklar

[57] ABSTRACT

A probe assembly system for high pressure insertion and retrieval in pressure vessels includes a stuffing box fitting with an integrally formed collet which surrounds a probe or device passing axially therethrough. The collet fingers are externally taper threaded and an internally taper threaded collet lock nut locks and releases the collet with minimal rotation. The interior of the collet fingers have teeth which bite into the shank of the probe or device. A single acting hand pump operated tool is quickly attached to the fitting. The tool includes a piston and cylinder with an elastic cord spring return inside the cylinder and attached to the piston in sling shot fashion. The lower end of the tool includes a socket for the collet lock nut which can be tightened and released by axial rotation of the tool. The lower end also includes a window and piston stop. The piston can be attached to the probe, if required. The hand pump includes a pressure gauge and variable relief valve. The entire system is portable and may be operated by one person.

18 Claims, 3 Drawing Sheets

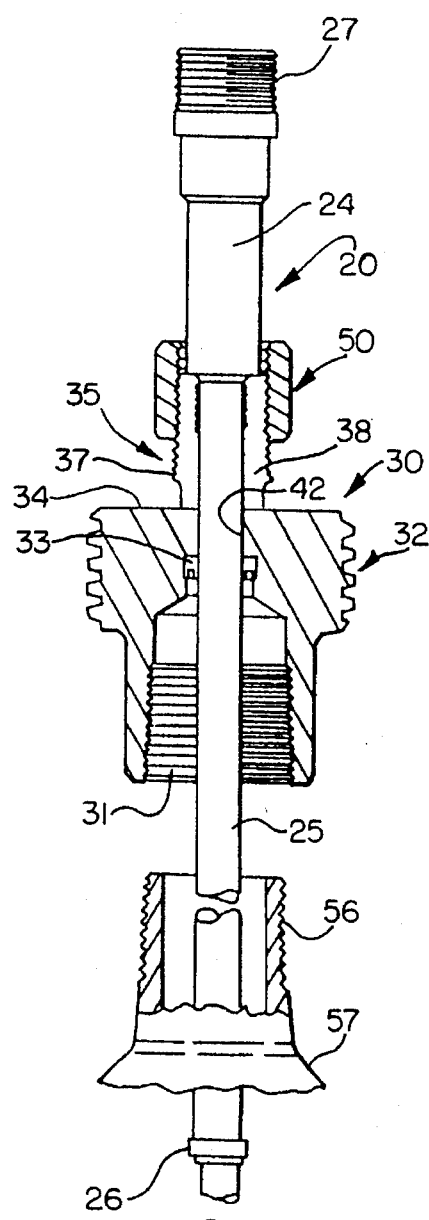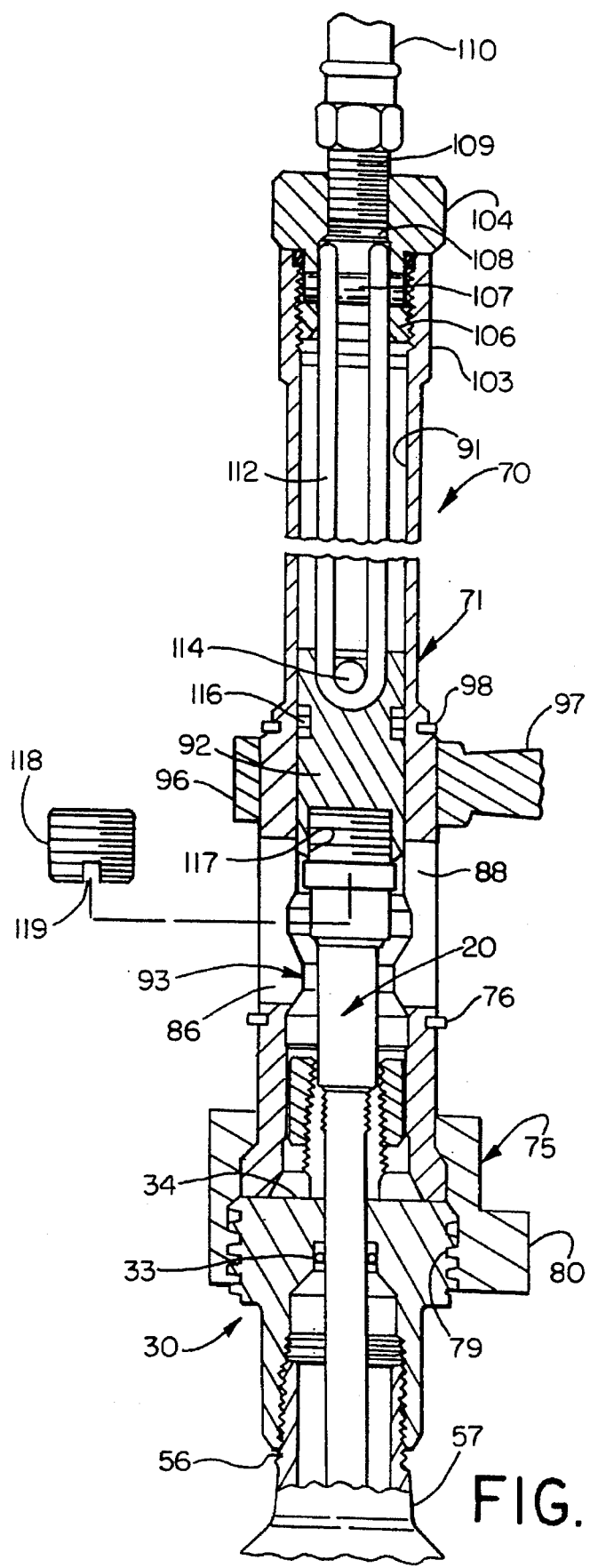

PROBE ASSEMBLY SYSTEM, INSERTION AND RETRIEVAL TOOL THEREFOR, AND METHODS

DISCLOSURE

This invention relates generally as indicated to a probe assembly system, and more particularly to probe assemblies or devices which are inserted in and removed from high pressure vessels and the like; to a tool therefor; and to methods of inserting and removing such devices.

BACKGROUND OF THE INVENTION

Probe assemblies or devices are often inserted in and removed from pressure vessels such as a pipeline for a variety of purposes. Such devices include, for example, corrosion coupons, corrosion probes, injection or sampling devices, and a wide variety of sensing, measuring and control devices. Sometimes the probe is threaded into a high pressure access fitting as seen in Applicants copending application Ser. No. 08/355,623, filed Dec. 14, 1994, and entitled High Pressure Access Fitting And Method.

Such probes are usually installed through a high pressure access valve by a high pressure retriever such as shown in Applicant's prior U.S. Pat. No. 4,537,071.

Probes or devices are also inserted or retrieved through sealed fittings such as a stuffing box or packer joint, and they are often done so with hydraulic tools or drives. Examples of hydraulic tools or drives are seen in U.S. Pat. Nos. 3,718,034, 3,812,722, 4,346,611, 4,387,592, 4,916,797, 4,930,361 and 5,385,060. Such tools are usually double acting, or if single acting rely solely on the pressure in the vessel for retrieval. Such tools usually require two people to complete the steps required. Cylinders with laterally extending fittings make the tool bulky and awkward and inhibit axial rotation of the tool, particularly once the tool is installed on a fitting. If a hydraulic spring return cylinder could be provided, the stroke of most conventional springs is far too short to have any range of applications, particularly since a stroke of a meter or more may be required in some applications. Moreover, the tools cannot quickly be attached to a probe containing stuffing box fitting, and then axially rotated with respect to the fitting to lock and unlock the probe with respect to the fitting.

Collets are widely used as gripping devices, and are sometimes employed in connection with the insertion and retraction of devices into and out of pressure vessels. Examples of such employment of collet, may be seen in U.S. Pat. Nos. 4,275,592, 4,697,465, 5,106,580, and 5,138,755. Such collets and any related fittings are usually characterized by complexity and are not capable of locking or unlocking a device simply by rotating a tool axially of the fitting to which it is attached.

It would, therefore, be desirable to have a tool and an associated simplified stuffing box fitting where the assembled tool can be used to lock or unlock the device with respect to the fitting by limited axial turning of the tool itself.

SUMMARY OF THE INVENTION

The high pressure access retrieval system includes both a probe and stuffing box assembly fitting as well as a simplified hydraulic tool which may quickly be attached to the fitting, and when attached, used both to lock or unlock the probe or device with respect to the stuffing box fitting, and insert or retrieve the device or probe through such fitting.

The probe assembly includes a stuffing box fitting which has an integrally formed axially projecting collet, the fingers of which have external tapered threads which mate with internal tapered threads of a collet lock nut. The fitting includes a high temperature and high pressure seal and the device extends axial therethrough. The collet may have internal teeth which bite into the shank of the device. The device includes a stop on its inner end and a shoulder on its outer end so that when assembled, the device and fitting cannot be separated without removing the stop.

The fitting is attached to an adapter nipple which includes a bleed valve, such nipple in turn being attached to an access valve, in turn attached to the vessel or pipe.

The exterior of the fitting is provided with relatively coarse threads which enables the hydraulic tool to be quickly attached to the fitting by a hammer union, for example, to extend axially thereof. The tool comprises an elongated body which may, for example, be about a meter or more in length. The tool body may rotate axially within the hammer union and axially of the stuffing box fitting. The inner end of the tool body includes a flatted socket which fits over the collet lock nut. The exterior of part of the inner part of the body is hexagonal and a relatively short laterally projecting handle meshes with the exterior of the body so that the entire tool may be rotated on its axis the few turns required to lock or unlock the collet nut. The inner end of the body also includes a window and a piston-stop within the window.

The outer end of the body and its major extent is cylindrical and accommodates the hydraulic piston for axial movement. The piston is single acting with a spring return. The spring return is an elastic cord which is attached to the outer end of the body or blind end of the cylinder and extends in U-shape or sling shot fashion around a diametral pin on the inside of the piston and a similar pin in the cylinder blind end cap. The elastic cord is within the hydraulic fluid cylinder and displaces a compatible hydraulic fluid.

The piston includes a threaded socket which may receive a button plug for pushing or engaging the probe or devices. Alternatively, the plug may be removed and the probe or devices may be threaded into the socket so that the piston and probe or device are attached. In this manner, the elastic cord may assist in the removal of a probe or device if the internal pressure in the vessel is inadequate to force the probe outwardly. When the piston is against the stop, it will be held against rotation, and the socket clear of the collet lock nut.

The outer end of the body has a single axially projecting hydraulic fitting which extends to an hydraulic hand pump. The pump includes a variable or adjustable relief valve, and a pressure gauge reading the output pressure of the hydraulic fluid. The pump and tool form a readily portable compact package.

The invention also includes the method of installing a probe by assembling the hydraulic tool to the stuffing box fitting in place on the vessel with the probe locked to the fitting. The piston is advanced to engage the probe under pressure, the probe is unlocked by rotating the tool a few turns, and the piston is further advanced to drive the probe to an insertion position through an access valve. The probe is relocked to the fitting, again by rotating the tool. The reverse procedure is employed to retrieve the probe or device, with the fitting and probe being removed after the access valve is closed and proper bleeding of pressure beyond the valve. During the retrieval process, the probe and piston may be attached to obtain a spring assist through the elastic cord. The pressure within the vessel is normally sufficient to drive the probe or device outwardly as the pressure behind the piston is gradually reduced through the variable pump relief valve.

To the accomplishment of the foregoing and related ends the invention, then, comprises the features hereinafter fully described and particularly pointed out in the claims, the following description and the annexed drawings setting forth in detail certain illustrative embodiments of the invention, these being indicative, however, of but a few of the various ways in which the principles of the invention may be employed.

BRIEF DESCRIPTION OF THE DRAWINGS

FIG. 1 is a sectional view of the probe or device assembled to the stuffing box fitting, partially broken away, and separated from the upper end of an adapter nipple;

FIG. 2 is an assembly in section of the tool and fitting threaded to the probe, the cylinder being broken away and greatly foreshortened, and the piston button plug shown removed;

DESCRIPTION OF THE PREFERRED EMBODIMENT

Figure 3:
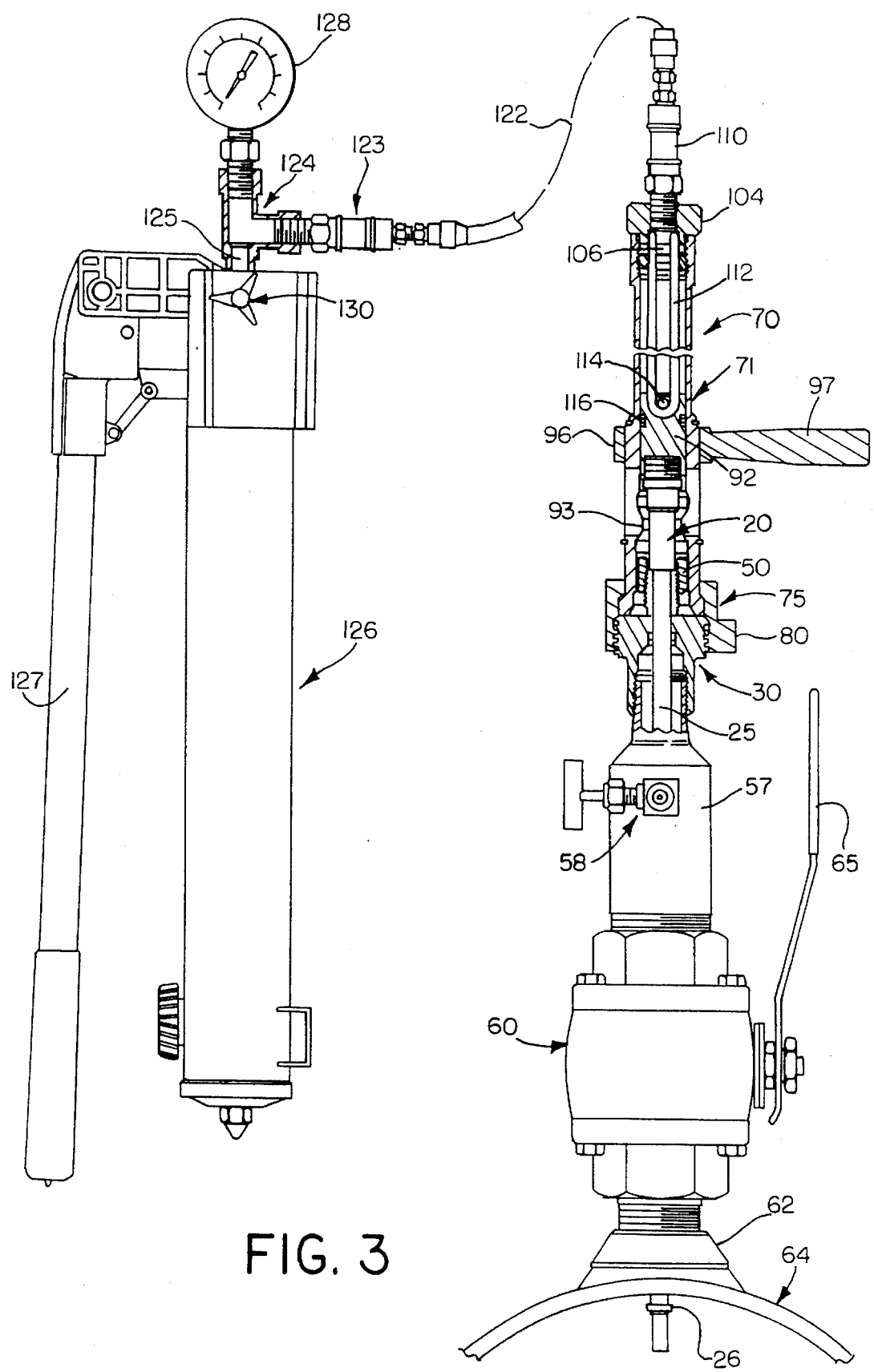
FIG. 3 is a complete assembly of the tool and fitting, partially broken away and in section.

Referring initially to FIGS. 1, 2 and 3, there is illustrated a probe or device shown generally at 20 which includes an upper enlarged shoulder 24, a shank 25, and a lower inner safety stop shoulder 26. The outer end of the probe or device is provided with relatively fine external threads as indicated at 27. The terms probe or devices is intended to cover a wide variety of such devices which are inserted in and removed from pressure vessels such as a pipeline for a wide variety of purposes. Such devices may include, for example, corrosion coupons, corrosion probes, injection or sampling devices, and a wide variety of sensing, measuring and control devices.

In FIG. 1, the probe assembly is shown assembled to and extending through a stuffing box fitting shown generally at 30. The stuffing box fitting includes inner internal tapered threads 31, an outer annular shoulder divided with coarse threads 32, and an internal high pressure and high temperature seal 33. The top of the shoulder has an annular flat surface 34 from which projects an integrally formed axially projecting collet shown generally at 35.

Figure 5:
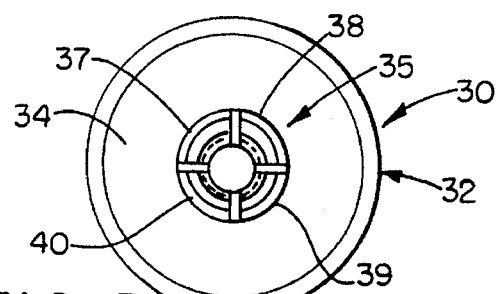
FIG. 5 is a top plan view of the stuffing box fitting.
Figure 4:
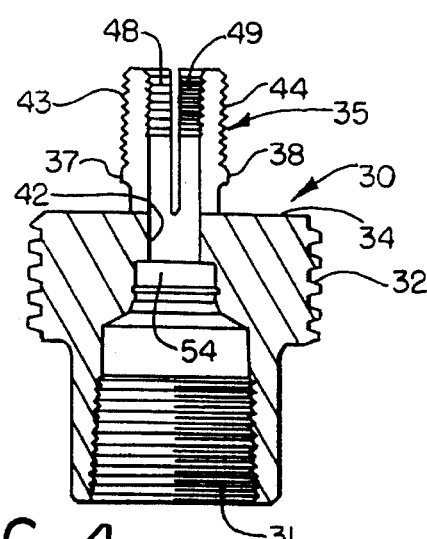
FIG. 4 is an enlarged axial section of the stuffing box fitting.
Figure 6:
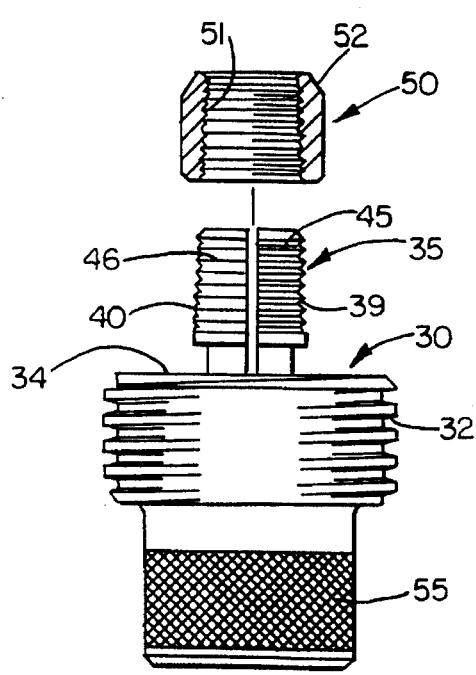
FIG. 6 is an exploded view of the stuffing box and collet lock nut.

Referring briefly to FIGS. 4, 5 and 6, the collet includes four axially projecting fingers 37, 38, 39 and 40. The fingers are quadrant paced around the central bore 42 which accommodates the shank of the probe or device. The exterior of each finger is provided with tapered threads as seen at 43, 44, 45, and 46, respectively. The interior of each collet finger is also provided with sharp teeth as seen at 48 and 49 in FIG. 4. These teeth bite into the shank of the device or probe when the collet is locked.

The collet is locked and unlocked with a few turns of collet lock nut 50 which has internal tapered threads 51 matching the external tapered threads on the collet fingers. The collet lock nut is also provided with a significant upper outer edge chamfer indicated at 52 for a purpose hereinafter described.

The body of the stuffing box as seen in FIGS. 4 and 6 include the interior annular shoulder 54 in which the high temperature/high pressure seal is mounted. The exterior of the body also may be knurled as indicated in FIG. 6 at 55.

Figure 7:
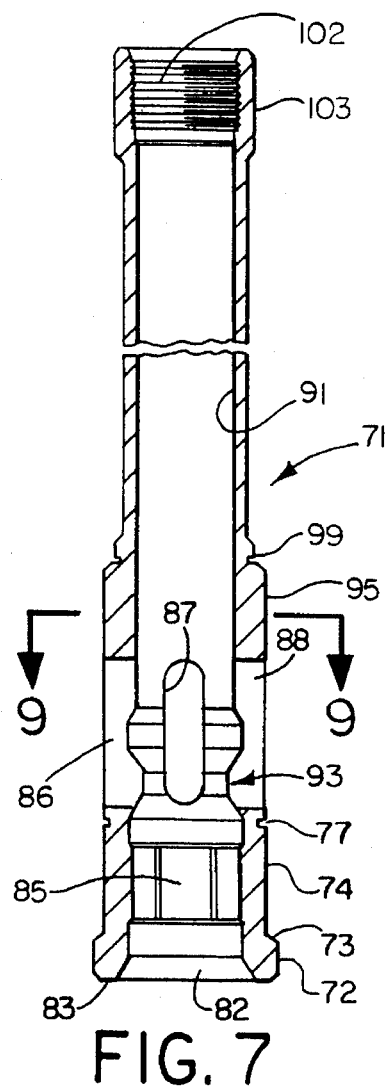
FIG. 7 is a broken sectional view of the tool body.
Figure 8:
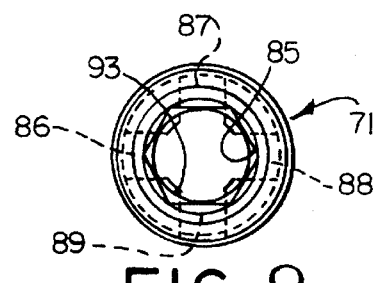
FIG. 8 is an inner end view of the tool body showing the, collet lock nut socket.

Referring back to FIGS. 1, 2, and more particularly to FIG. 3, it will be seen that the stuffing box fitting 30 has threaded on matching threads 56 on the outer end of an adapter nipple 57 which includes a bleed valve 58. The adapter nipple is mounted on the outer end of access valve 60 which is turn mounted on high pressure fitting 62 on the pressure vessel 64 which may be in the form of a large diameter pipe. The valve includes an operating handle 65 which is shown in the open position. The probe is shown projecting through the open valve into the Referring now more particularly to FIGS. 2, 3 and FIGS. 7–9, there is illustrated a single acting hydraulic spring return insertion and retrieval tool 70 for inserting and retrieving the probe or device assembly seen more clearly in FIG. 1. The tool 70 comprises an axially elongated body shown generally at 71. The body seen more clearly in FIG. 7 is in the form of an elongated tubular member. Depending upon the size of the vessel and the probes or devices involved, the body may be substantially elongated and have an overall length dimension of approximately a meter or more. The inner end of the body is provided with an exterior flange indicated at 72. The flange provides a sloping exterior shoulder 73 at the inner end of cylindrical exterior surface 74 which accommodates a hammer union 75, seen in FIGS. 2 and 3. The hammer union rotates freely on the inner end of the tool body and is held in place in assembled condition with the body by a snap ring 76 which fits within slot 77. The hammer union has interior coarse threads 79 on its lower projecting end which mate with the exterior coarse threads 32 on the stuffing box assembly 30. The hammer union is also provided with radial projections indicating at 80 which enable the hammer union to be rapped by a hammer.

The lower end of the interior of the tool body is provided with a significant bevel indicated at 82. The surface 82 acts as a pilot surface to enable the tool quickly and easily to be placed over the collet lock nut 50 so that the annular end 83 of the tool body is close to the annular top shoulder surface 34 of the stuffing box fitting.

The interior of the inner end seen at 85 is a flatted socket adapted to mate with the exterior of the collet lock nut 50. The tool body is thus in the form of a socket wrench, and the socket 85 is adapted to fit the collet lock nut 50.

Immediately beyond the lock nut socket 85, the tool body is provided with four quadrant spaced axially elongated windows seen at 86, 87, 88, and 89. Such windows are shown in dotted lines in FIG. 8.

Outwardly of the windows, the tool body forms a polished uniform diameter cylinder 91 which accommodates hydraulic piston 92 for axial sliding movement therein. Within the axial reach of the windows near their inner ends, there is provided a piston stop shown generally at 93. Piston stop is simply a tapered inward projection from the diameter of the cylinder of the assembly and would be annular, but for the interruption by the windows.

Figure 9:
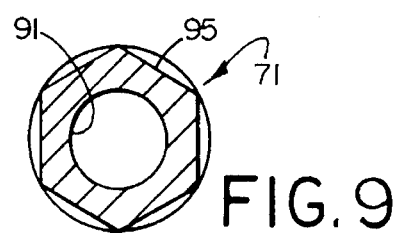
FIG. 9 is a transverse section of the body taken substantially on the line 9—9 of FIG. 8.

The exterior of the body outwardly beyond the windows is provided with hexagonal flats seen more clearly at 95 in FIG. 9. Such flats interfit with interior flats in the hub 96 of handle 97. The handle is held in place by snap ring 98 fitting within groove 99. Accordingly, the handle may readily be assembled over the outer end of the tool and secured in place by the noted snap ring. With the handle, the tool may readily be rotated around its elongated axis.

The outer end of the tool body includes internal threads 102 in the somewhat enlarged wall thickness end 103, such threads accommodating cylinder end cap assembly 104. The end cap assembly 104 includes an externally threaded inwardly projecting skirt 106. A dowel pin 107 extends diametrically of the skirt. The end cap assembly is provided with, an axially extending threaded hole 108 which accommodates hydraulic hose fitting 109 extending axially of the tool as indicated at 110 in FIGS. 2 and 3. Extending around the dowel pin 107 is a continuous elastic shock cord or bungee tube or cord 112.

The shock cord also extends around diametral dowel pin 114 in piston 92. Accordingly, there are four strands of the continuous elastic shock cord extending between the end cap assembly 104 and the piston 92, all within the cylinder 91. The hydraulic fluid employed should be compatible with the material of the elastic shock cord. Anytime the piston moves away from the end cap assembly, the shock cord elastically elongates creating a return force which increases with the distance between the end cap assembly and the piston.

The piston includes the sliding seals 116 seen in FIGS. 2 and 3, and that its lower end includes a threaded socket 117 which normally receives button plug 118. The outer end of the plug is provided with a transverse slot seen at 119 in FIG. 2. The button plug may easily be inserted or removed by a screw driver projecting through the inner end of the tool when the piston is extended against the stop 93. Alternatively, as seen in FIGS. 2 and 3, the piston 92 may be threadedly attached to the outer threaded end 27 of the probe or device as hereinafter described.

Referring now to FIG. 3, it will be seen that the axially extending fitting on the outer end of the tool is connected to hydraulic hose 122 connected through fitting 123 to one end of street tee 124 connected to the output 125 of hand operated hydraulic pump 126. The pump handle is shown at 127. The other end of the street tee is connected to pressure gauge 128. The pump includes a variable manually operated relief valve 130. The hose may be about three meters in length and the pump hose and tool may be bundled together to form a readily portable package easily handled and operated by a single person. The hose fittings are such that they may readily be connected and disconnected without loss of hydraulic fluid.

For insertion, the access valve will be closed, the probe or device and stuffing box will be assembled in a retracted position so that when the stuffing box is assembled to the adapter nipple, the inner end of the probe will clear the closed valve. The collet lock nut will be latched, and the collet latch will lock the shank of the probe or device to the stuffing box fitting. The dust cover and safety clamp are removed from the probe end. At this point, the tool is installed on the stuffing box fitting 30 as seen in FIGS. 2 and 3, with the end of the tool forming an axial extension of the fitting and being close to the flat annular transverse bearing surface 34 of the stuffing box fitting. The tool is installed simply by tightening the hammer union. Next, the hydraulic hose may be attached between the pump and tool. With the pump relief valve in the closed position, the pump handle is then operated to extend the piston against the retraction pressure of the elastic shock cord. When the piston engages the probe projecting from the stuffing box fitting, the pressure shown on the gauge will start to go up. This indicates that the probe is now being backed by the piston.

At this point, the access valve is now open slowly to pressurize the fitting. After pressurizing the fitting, the handle 97 is employed to rotate the tool a few turns on its axis counterclockwise looking inwardly to release the collet lock nut permitting the collet fingers to disengage from the probe shank. The probe can now be installed into the system through the now open access valve simply by using the pump. The windows in the tool body may be employed to verify that the probe is at the correct insertion depth. This can often be done simply by measuring and marking the probe which mark will become visible as it moves into the window. When at the correct insertion depth, the tool is then rotated clockwise using the handle 97 to lock the collet in place. The operator should verify that the collet is holding the probe in the inserted position by opening the relief valve. As the relief valve is opened, the probe should not move. Once it is verified that the collet is properly holding the probe in place, the tool can now be removed from the system by unlatching the hose and backing off the hammer union. The operator must then reinstall the safety clamp kit and the dust cover.

The reverse procedure is employed to retract the probe. With the tool installed and the pump connected, the probe is backed by the piston under pressure. The probe can then be retracted from the system. The operator rotates the tool counterclockwise a few turns to release the probe from the collet. The operator then slowly opens the relief valve on the pump to retract the probe from the system. The pressure differential between the vessel and the hydraulic system is normally enough to force the probe outwardly. Once the probe is clear of the access valve, the access valve is closed. At this point, the bleed valve 58 is slowly opened. When the pressure between the fitting and the valve is bled down, the tool can now be removed from the fitting and the fitting which includes the probe or device removed from the valve nipple 57.

In the event that the probe does not retract into the tool, it may become necessary to attached the probe or device to the piston. The operator rotates the tool a few turns clockwise to relock the collet retaining the probe. The operator then opens the relief valve to verify that the collet is holding. The operator then closes the relief valve and removes the tool from the fitting. The operator then pumps the piston to the front of the tool until it contacts the stop 93. Because of the configuration of the stop, the stop will keep the piston from rotating. Then using a large slotted screw driver from the inner end of the tool, the plug 118 may readily be removed. With the plug removed, the operator places the tool over the probe and threads the tool piston onto the probe by rotating the entire tool clockwise. It is noted that with the piston extended and locked against the stop 93, the collet lock nut socket 85 is well above the collet lock nut. The socket can engage the collet lock nut only when the piston is retracted and the hammer union is able to engage the stuffing box fitting.

After the tool piston is secured to the probe or device, the operator may then open the relief valve which will cause the tool to be pulled over the probe and onto the fitting. After the hammer union is tightened, the operator again closes the relief valve to ensure that the probe is backed by hydraulic pressure. The operator may then rotate the tool a few turns counterclockwise to release the collet latch holding the probe. The probe can now be pulled up into the tool by opening the relief valve slowly. At this point, the internal pressure of the vessel as well as the force of the elastic shock cord is acting on the probe. Once the probe clears the access valve, such valve is closed. The pressure between the access valve and fitting is then bled down. The fitting and the probe or device can now be removed from the valve nipple along with the tool. The operator closes the relief valve and removes the hammer union from the fitting. The operator then pumps the piston to the stop which then holds the piston against rotation. This permits the operator to unscrew the probe from the piston.

It can now be seen that there is provided a high pressure access retrieval system including both the probe and stuffing box assembly fitting as well as a simplified hydraulic tool which may be quickly be attached to the fitting, and when attached, used both to lock or unlock the probe or device with respect to the stuffing box fitting, and insert or retrieve the device or probe through such fitting. The tool acts both as a socket wrench for the fitting and as a hydraulic tool for inserting or retrieving the probe or device to or from the pressure vessel.

Although the invention has been shown and described with respect to certain preferred embodiments, it is obvious that equivalent alterations and modifications will occur to others skilled in the art upon the reading and understanding of this specification. The present invention includes all such equivalent alterations and modifications, and is limited only by the scope of the claims.

What is claimed is:

1. A probe assembly for a high pressure access retrieval system comprising a stuffing box fitting having a sliding high pressure seal, a probe having a shank inserted axially through said fitting for sliding movement therethrough, said fitting including an integrally formed collet projecting axially and surrounding the shank of the probe, said collet including external tapered threads, and a nut having internal tapered threads in engagement with said external tapered threads of said collet whereby said collet may be tightened firmly to grip the shank of the probe at a selected position axially of the fitting by tightening the nut.

2. A probe assembly as set forth in claim 1 including teeth on the interior of the collet operative to bite into the shank of the probe when said nut is tightened.

3. A probe assembly as set forth in claim 1 including a stop on the inner end of said probe precluding the movement of said probe outwardly through said stuffing box.

4. A probe assembly as set forth in claim 1 including threads on the inner end of said fitting adapted to secure said fitting to a pressure vessel through an access valve.

5. A probe assembly as set forth in claim 1 including threads on said fitting adapted to secure an insertion and removal tool to said fitting.

6. A probe assembly as set forth in claim 5 including said tool, and wherein said tool is rotatable on the axis of said fitting and includes a nut socket operative to engage said nut.

7. A probe assembly as set forth in claim 6 wherein said tool includes a hydraulic piston for insertion and removal of said probe when said nut is loosened.

8. A probe assembly as set forth in claim 7 wherein said tool includes a handle projecting laterally of said tool.

9. A probe assembly as set forth in claim 8 wherein said piston is single acting and has a spring return.

10. A probe assembly as set forth in claim 9 wherein the spring return comprises an elastic cord within the cylinder.

11. A probe assembly as set forth in claim 10 wherein said elastic cord is attached to the piston as a sling shot.

12. A probe assembly as set forth in claim 11 including a hand operated hydraulic pump for said tool, said pump including an output pressure gauge and an adjustable relief valve.

13. A probe assembly as set forth in claim 12 including a window in said body, and a piston stop in said window operative to keep the piston from rotating.

14. A probe assembly as set forth in claim 13 including means operative optionally to attach the piston and probe when the piston is against the stop to enable the spring return to pull the probe through the stuffing box, said socket being clear of said nut when said piston is against the stop.

15. In combination, a pressure vessel, a probe assembly for said pressure vessel, an access valve secured to said vessel, and a stuffing box fitting secured to said access valve, said stuffing box fitting including an outwardly extending integrally formed collet, and a probe gripped by said collet projecting through said stuffing box fitting, through said access valve, and into said pressure vessel.

16. The combination set forth in claim 15 including a nut threaded on said collet operative to tighten or loosen said collet.

17. The combination set forth in claim 16 including retrieval tool means operative to tighten or loosen said nut when said tool means is secured to said fitting and in axial alignment therewith.

18. The combination set forth in claim 17 wherein said nut has internal tapered threads matching external tapered threads on said collet.

\* \* \* \* \*

UNITED STATES PATENT AND TRADEMARK OFFICE
CERTIFICATE OF CORRECTION

PATENT NO.  : 5,621,181
DATED       : April 15, 1997
INVENTOR(S) : David K. Waterman It is certified that error appears in the above-indentified patent and that said Letters Patent is hereby corrected as shown below:

> On the title page, item [73], should read:
> -- Rohrback Cosasco Systems, Inc.
>    Santa Fe Springs, California --

Signed and Sealed this

Twenty-first Day of October 1997

Attest:

BRUCE LEHMAN

Attesting Officer

Commissioner of Patents and Trademarks